United States Patent [19]

Kennedy et al.

[11] Patent Number: 4,752,468

[45] Date of Patent: Jun. 21, 1988

[54] **METHOD OF CONTROLLING PLANT FEEDING MITES WITH THE FUNGUS *NEOZYGITES FLORIDANA***

[75] Inventors: George G. Kennedy, Apex, N.C.; David R. Smitley, Okemos, Mich.

[73] Assignee: North Carolina State University, Raleigh, N.C.

[21] Appl. No.: 882,827

[22] Filed: Jul. 7, 1986

[51] Int. Cl.$^4$ .............................................. A01N 63/00
[52] U.S. Cl. ..................................... 424/93; 435/254; 435/911
[58] Field of Search .................... 424/93; 435/911, 254

[56] References Cited

U.S. PATENT DOCUMENTS 4,021,306  5/1977  Soper, Jr. .................. 435/254 X
4,530,834  7/1985  McCabe et al. .................. 424/93
4,668,512  5/1987  Lewis et al. .................. 424/93

OTHER PUBLICATIONS

David R. Smitley Thesis, An Entomogenous Fungus, *Neozygites Floridana* Weiser and Muma; Mite Aerial Dispersal; and Environmental Conditions as Factors in Population Declines of the Twospotted Spider Mite, *Tetranychus Urticae* Koch (1985), pp. 1-112.

R. A. Humber, G. J. Moraes and J. M. Dos Santos, *Entomophaga* 26, 421-425 (1981).

J. Weiser and M. H. Muma, *Florida Entomologist* 49, 155-159 (1966).

C. W. McCoy and T. L. Couch, *Florida Entomologist* 65, 116-126 (1982).

R. L. Brandenburg and G. G. Kennedy, *Journal of Economic Entomology* 75, No. 4, 691-694 (1982).

R. L. Brandenburg and G. G. Kennedy, *Journal of Economic Entomology* 74, No. 4, 428-431 (1981).

G. R. Carner and T. D. Canerday, *Journal of Economic Entomology* 63, No. 2, 638-640 (1970).

R. Kenneth, G. Wallis, U. Gerson and H. N. Plaut, *Journal of Invertebrate Pathology* 19, 366-369 (1972).

G. R. Carner, *Journal of Invertebrate Pathology* 28, 245-254 (1976).

R. L. Bradenburg and G. G. Kennedy, *Ent. Exp. & Appl.* 34, 240-244 (1983), *Ned. Entomol. Ver. Amsterdam*.

L. S. Boykin, W. V. Campbell and M. K. Beute, *Journal of Economic Entomology* 77, No. 4, 969-975 (1984).

A. G. Selhime and M. H. Muma, *The Florida Entomologist* 49, No. 3, 161-168 (1966).

H. Nemoto, M. Kobayashi and Y. Takizawa, *Appl. Ent. Zool.* 14 (4), 376-382 (1979).

*Primary Examiner*—Howard E. Schain
*Attorney, Agent, or Firm*—Bell, Seltzer, Park & Gibson

[57] ABSTRACT

A method of selectively controlling plant feeding mites in the family Tetranychidae, such as the Twospotted spider mite (*Tetranychus urticae*), is disclosed. The method comprises innoculating an agricultural field containing crop plants with a Neozygites fungus which selectively infects plant feeding mites without infecting other insects. The population of plant feeding mites is thereby reduced to a level at which they cannot substantially damage the crop plants.

16 Claims, No Drawings

METHOD OF CONTROLLING PLANT FEEDING MITES WITH THE FUNGUS *NEOZYGITES FLORIDANA*

TECHNICAL FIELD

This invention relates to methods for controlling insect pests generally, and particularly relates to a method of controlling plant feeding mites with a fungus which selectively kills the mites.

BACKGROUND OF THE INVENTION

There are two serious side effects which result from the use of most modern insecticides: the development of insect resistance to the treatment, and the nonspecific and broad-ranging killing effect of many such insecticides. These two side effects can, moreover, interact with one another to exacerbate the obvious practical problems they cause. When a broadly toxic insecticide is used to control a few specific insect pests, many of the other nontargeted insects affected by the treatment can develop resistance to it even though there was no need to kill them. Later, when there is a need to control the previously nontargeted insects, they will have likely become resistant to the insecticide to which they were previously exposed, and one option for their control will have been rendered useless. A considerable amount of research has accordingly been directed, and continues to be directed, towards solving these problems. See generally L. B. Brattsten, et al., Insecticide Resistance: Challenge to Pest Management and Basic Research, 231 *Science* 1255 (14 Mar. 1986).

There has been some interest shown in using fungi to control insect pests. For example, *Hirsutella thompsonii* has been suggested as a fungus useful as a mite control agent, (or a "mycoacaricide") in citrus rust mites. See, e.g., C. W. McCoy and T. L. Couch, 65 *Florida Entomologist* 116 (1982). It has been suggested that other types of fungi, such as fungi in the genus Entomophthora, might be useful as mycoacaricides because of the role they are believed to play in nature (See U.S. Pat. No. 4,021,306 to Soper; see also, U.S. Pat. No. 4,530,834 to McCabe), and there has been a considerable amount of basic research on the natural effects of these fungi on insect populations--including studies of the role of the fungus *Neozygites floridana* in regulating the population of various plant feeding mites. Exemplary of this research are R. L. Brandenburg and G. G. Kennedy, 34 *Ent. Exp. and Appl.* 240 (1983), R. L. Brandenburg and G. G. Kennedy, 74 Journal of Economic Entomology 428 (1981), and L. S. Boykin, W. V. Campbell and M. K. Beute, 77 *Journal of Economic Entomology* 969 (1984). This research has not brought forth a significant number of new mycoacaricides which can actually be applied to agricultural crops, or mycoacaricides which can confidently be said to be highly specific and selective in their action, even though there is a continuing need for such new, commercially useful, insect control agents.

DESCRIPTION OF THE INVENTION

In an agricultural field containing crop plants, which field is infested with both insects which do not significantly harm the crop plants and undesirable plant feeding mites, we herein disclose a method of selectively reducing the population of the plant feeding mites. The method comprises innoculating the field with an amount of the fungus *Neozygites floridana* (*N. floridana*) effective to infect the plant feeding mites. As a result of this treatment, the plant feeding mites are selectively killed without substantially infecting the insects which are not harmful to the crop plants. The agricultural field may be located outside, or within a greenhouse. Preferably the field is innoculated with an amount of *N. floridana* effective to reduce the population of plant feeding mites to a level at which they cannot substantially damage the crop plants.

The plant feeding mites which can be selectively killed by our method belong to the family Tetranychidae in the Suborder Trombidiformes in the Order Parasiti. Exemplary of the genera of mites within the Tetranychidae family which can be selectively killed by our method are mites in Genus Eutetranychus, Genus Panonychus, Genus Tetranychus, Genus Oligonychus, and Genus Eotetranychus. Exemplary of particular species of mites within the family Tetranychidae which can be selectively killed by the method of the present invention are the Six-spotted spider mite (*Eotetranychus sexmaculatus*), the Texas citrus mite (*Eutetranychus banksi*), the Citrus red mite (*Panonychus citri*), the European red mite (*Panonychus ulmi*), the McDaniel mite (*Tetranychus mcdanieli*), the Pacific spider mite (*Tetranychus pacificus*), the Strawberry spider mite (*Tetranychus turkestani*), the Twospotted spider mite (*Tetranychus urticae*), the Spruce spider mite (*Oligonychus ununguis*), the Sugi Spider mite (*Oligonychus hondoensis*), and *Tetranychus evansi*.

These plant-feeding mites cause damage to a wide variety of crops. For example, in the United States, crops which suffer significant damage from Twospotted spider mites include Citrus, Grape, Almond, Pome Fruits, Pecan, Stone Fruits, Wheat, Strawberry, Vegetable Crops, Peanut, Cotton, Corn, and ornamental and forestry crops.

An important advantage of our invention is the selectivity of its killing action. We have extensively studied the effects of *N. floridana* on predatory insects, and have consistently found them to resist infection. Among the predatory insects we have found to resist *N. floridana* infection are Cecidomyiid larvae (a fly), Geocoris sp. (Big eyed bug), Orius spp. (minute pirate bug), Hemerobiid larvae (brown lacewing), Crysopa larvae (green lacewing), Coleomagilla spp. and Hippodamia spp. larvae (ladybird beetle larvae). The method of the present invention is so selective that even species of mites which are predatory, rather than plant feeding, are not infected. We have particularly observed several species of predaceous mites in the genus Neoseiulus to be unaffected by *N. floridana*. Further, in one hundred attempts to infect *Neoseiulus fallacis* with *N. floridana* in the laboratory, we observed no infection. Similarly, we were unsuccessful in infecting another predaceous mite, *Phytoseiulus persimilis*, despite 100 attempts in a laboratory study.

*Neozygites floridana* also has been called *Entomophthora floridana* and *Triplosporium floridana*. This fungus was previously isolated by Jaroslav Weiser and Martin H. Muma, who found it in Texas Citrus Mites (*Eutetranychus banksi*) on citrus, in Lake Alfred, Fla. U.S.A., and was identified and described in their paper entitled "*Entomophthora floridana* N. Sp. (Phycomycetes: Entomophthoracea), A Parasite of the Texas Citrus Mite, *Eutetranychus banksi*," in *The Florida Entomologist*, 49(3), 155-159 (1966). See also A. G. Selhime and M. H. Muma, Biology of *Entomophthora floridana* attacking

*Eutetranchus banksi, The Florida Entomologist*, 49, (3) 161–168 (1966). The fungus can be described as it was described by Weiser and Muma: it has mycelia which are divided into short tubular or club-shaped hyphal bodies, with two to four nuclei, that grow into curved and obtuse segments which are mostly unbranched. The mycelia are found distributed throughout the host mite's body. Root-like hyphae grow through the cuticle of the host to form slightly broadened conidiophores outside the host body. The conidiophores are sometimes curved, and are single, 30 to 35 microns by six to eight microns, and grow from root-like hyphae of the same length which are only three to four microns wide. Numerous refringent granules, fat droplets or starch, are seen in the conidiophores. The hyphal protoplasm is hyaline, without granules in the septal region. The septum is formed at the periphery of the conidiophore.

The conidia are pyriform, papillate, subpapillate, or epapillate type, and 13 to 18 microns by 11 to 13 microns, averaging 12 by 15 microns with the basal end five to six microns wide. The Conidia have four sperical nuclei and refringent granules of fat and starch. Weiser and Muma observed that these structures are not stained by cotton blue in Amman's solution. The conidiophores have persistent columellae, not bursting during the spore discharge. There is no gelatinous substance on the surface of conidia. Prior to discharge, both the membranes of the columella and that of the conidium are flat, rather than inflated. In fixed mounts, conidia on conidiophores are similar to the truncata type of Lakon's classification. Lakon, G., *Z. Angew. Ent.* 5, 161 (1919). Secondary conidia are formed from primary conidia by a single, lateral, hyphal bud. Primary and secondary conidia are of the same size and shape. Microconidia have not been observed.

Anadhesive spores are produced by primary and secondary conidia at the ends of thin threads which measure 1.5 microns by 50 to 60 microns. These threads, which are curved adjacent to the anadhesive spore, retain a remnant of the conidial membrane at the opposite end. Mature anadhesive spores are claviform, measuring 15 to 20 microns by 10 to 12 microns. At the narrow end is a knob-like apex 1.5 microns wide. Anadhesive spores have a brownish striated cuticle; the apex seems to be adhesive because almost all anadhesive spores become attached to host mite setae and cuticle at this end. Primary anadhesive spores produce secondary anadhesive spores at the end of a capillary tube.

Resting spores, seldom seen in field collected material, are spherical or subspherical with a smooth thin three-layered wall. The upper wall of the resting spore has a rounded foramen at the former connection with the hypha. Resting spores have small refringent globules distributed throughout the protoplasm, but no oil globules or vacuoles. The resting spores are 20–23.5 by 22–26 microns in diameter, with the wall only 0.5 microns thick, and the foramen four microns in diameter. Weiser and Muma, supra, accompany their description with a complete set of illustrations.

This fungus has been found in other mites, in other locations, by other workers. For example, Hisaski Nemoto and Joji Aoki reported finding it attacking the Sugi Spider mite (*Oligonychus hondoensis*) in a plantation of Japanese cedar in the Kyushu District of Japan. H. Nemoto and J. Aoki, *Applied Entomology and Zoology* 10, 90 (1975).

Other species of Neozygities fungi known to be pathogenic on spider mites and expected to be useful in the present invention are *Neozygites tetranychi* and *Neozygites adjarica*. However, the classification of this group of fungi is not fully settled and these species may ultimately be grouped together as a single species under the name *Neozygites floridana*, grouped together under some other name, or further split into additional species. To describe our invention as best we are able, we have herein used the name "*Neozygites floridana*" for the fungus, or group of fungi, most useful in carrying it out. This term is therefore to be considered as descriptive of our invention, rather than limiting, and to encompass all equivalent fungi.

In the Southeastern United States, *N. floridana* can be found in association with populations of *Tetranychus urticae*. The best way to collect *N. floridana* is to locate dense populations of *T. urticae* on crop or feral host plants, and to collect several hundred mites during a period when temperatures range from 60 to 75 degrees Fahrenheit and of high relative humidity or immediately following a period of prolonged rain (two to three days). The mites should be kept alive on foliage of the plants from which they were collected. After five to seven days any infected mites will die and form the mummies characteristic of *N. floridana* infected mites. As long as the mummies are held at a relative humidity lower than 90 percent no sporulation of the fungus will occur.

Any mummies produced can be used to infect additional mites by placing them on foliage with healthy mites and holding them under conditions of 100 percent relative humidity and at a temperature of 70 degrees Fahrenheit for 72 hours.

We started a laboratory culture of *N. floridana* from infected *T. urticae* collected in peanut fields located in Chowan County, North Carolina. A stock culture was generated by exposing batches of spider mites raised on lima beans (cv. 'Henderson Bush') to infective spores (capillaconidia) produced from the original group of 20 infected mites. Additional infected mites were generated from the stock culture by placing one cadaver in the center of a bean leaf disc (1.5 cm dia) maintained on moist cotton in a Petri dish. The dish was covered, sealed in a plastic bag and held at 21.1 degrees Centigrade for 48 hours to allow the fungus to sporulate. Fifty to 100 spider mites were then added to the leaf disc. The bean leaf disc with the spider mites was held for an additional 24 hours under moist conditions before it was placed on fresh whole bean leaves maintained on moist cotton under normal laboratory conditions (25 degrees Centigrade, 30 percent relative humidity). Infected mites became brown cadavers in the lab within five days. All cadavers were stored over calcium carbonate in a four degrees Centigrade incubator or in a freezer until they were needed for experiments.

Infection of live mites can be verified by placing mites in a drop of lacto-phenol cotton-blue stain on a microscope slide and covering them with a cover slip. The mites should then be squashed by pressing down on the cover slip. Infected mites will extrude fungal hyphae which stain blue.

The foregoing procedures are used to collect sufficient numbers of insect mummies which have been infected and killed by the fungus, and which contain unsporulated *N. floridana*, to innoculate an agricultural field containing crop plants. The field can be innoculated by forming an aqueous suspension of such insect mummies, and spraying them on the crop plants.

The precise number of insects which should be sprayed on the crop will vary from crop to crop, with the degree of mite infestation in the field, and according to the speed at which it is desired to cause the mite population to crash. Killed insects should preferably be held in the aqueous suspension for no longer than about three to four hours, so that they will not sporulate and become unviable.

Any of a number of well-known stickers and other adjuvants may be advantageously included in the aqueous suspension of insect mummies. Exemplary of such adjuvants are Agar, "CELLOSIZE" from the Union Carbide Co., "DAEAGIN" and "FLO-GEL 1000" from the Diamond Shamrock Co., "MILLER-AIDE" and "NU-FILM 17" from the Miller Chemical and Fertilizer Corp., oils such as FC-435 from the Sun Oil Co., "ORTHO X-77" from the Chevron Chemical Co., "PYLAC" from the Hopkins Agricultural Chemical Co., and "TRITON B-1956" and "TRITON X-100" from the Rohm and Haas Co. Those skilled in the art will be aware of many other standard adjuvants which may also be used to advantage when practicing the present invention.

EXAMPLE 1

A series of field tests were carried out to demonstrate the effect of applying *N. floridana* to Two-spotted spider mites in corn. The results of these tests are summarized in Table 1, which shows that effective mite control was achieved by the present invention.

These data were generated by applying Twospotted spider mite "mummies" in an aqueous suspension (water plus one percent agar) at the rate of 2000 mummies per 10 feet of corn row. This rate of application provided good control with corn, but lower rates could be used on most other row crops and many tree crops because the closed nature of the crop canopy of most crops would be expected to sustain a higher relative humidity near the leaf surface of the plants than the rather open corn canopy.

Those skilled in the art will appreciate that environmental factors, such as temperatures and humidity, affect the production of primary and secondary conidia and capillaconidia in fungi such as *N. floridana*. This example demonstrates that the fungus, after it has been applied to an agricultural field infested by plant feeding mites, can be exposed to periods of sufficient length and of sufficiently high humidity for the mites to become infected, by irrigating the field and thereby wetting the foliage and soil in the field (see Table 1, footnote 3).

TABLE 1

Effect of applying *Neozygites floridana* Inoculum[1] on *T. urticae* populations on corn, Clayton, North Carolina, 1985.

| | Number of *T. urticae*/5 corn leaves/plot[2,3] | | | | | |
|---|---|---|---|---|---|---|
| | July 15, 1985 Pre-Inoculation | | July 22, 1985 1-week Post-Inoc | | July 26, 1985 2-Week Post-Inc | |
| Replicated | Treated | Untreated | Treated | Untreated | Treated | Untreated |
| 1 | 4128 | 3784 | 2976 | 4128 | 12 | 3744 |
| 2 | 5360 | 4228 | 5610 | 6144 | 96 | 4640 |
| 3 | 4790 | 5212 | 2388 | 5196 | 120 | 2448 |
| 4 | 3996 | 4448 | 3048 | 3768 | 268 | 1520 |
| 5 | 4544 | 3978 | 1512 | 4332 | 182 | 2738 |
| x | 4564 | 4330 | 3107 | 4713 | 135 | 3018 |

| | Percent *N. floridana* Infection | | | | | |
|---|---|---|---|---|---|---|
| | July 15, 1985 Pre-Inoculation | | July 22, 1985 1-week Post-Treat | | July 26, 1985 2-week Post-Treat | |
| Replicate | Treated | Untreated | Treated | Untreated | Treated | Untreated |
| 1 | 0 | 0 | 43 | 0 | 84 | 48 |
| 2 | 0 | 0 | 33 | 2 | 90 | 36 |
| 3 | 0 | 0 | 37 | 4 | 88 | 54 |
| 4 | 0 | 0 | 29 | 10 | 66 | 42 |
| 5 | 0 | 0 | 48 | 2 | 92 | 38 |
| x | 0 | 0 | 38 | 3.6 | 84 | 43.6 |

[1]Innoculum applied July 15, 1985 at rate of 2000 mummies per plot:
[2]Plots = 1 row × 10 feet
[3]Plots irrigated with one inch of water three days per week beginning July 13, 1985.

EXAMPLE 2

A series of laboratory experiments were conducted to explore the role of temperature and humidity on the production of primary and secondary conidia, infection, and pathogenesis of *N. floridana* on the Two-spotted spider mite. As will be explained in detail below, these data indicate that the production of primary and secondary conidia of *N. floridana* was greatest at 100 percent relative humidity, and that conidial production declined sharply as the relative humidity dropped below 98 percent. However, care must be exercised in extrapolating these results to field conditions, as the relative humidity near the leaf surface (within 1.0 cm) may differ considerably from the ambient relative humidity when dealing with field plants.

Experimental chambers for studying the relative humidity and temperature effects on the production of conidia were constructed by permanently gluing a 5.5 cm Petri dish inside of a 9.0 cm dish. Notches were cut along the top of the inner dish to allow adequate air flow to the inner chamber. The relative humidity of the inner chamber was controlled by filling the area between the inner and outer dish with saturated salt solutions prepared and used as described by Winston and Bates, *Ecology* 41, 232 (1960). The following salt solutions were chosen to maintain each relative humidity specified: NaCl (70 to 75 percent); KCl (80 to 85 percent); $K_2SO_4$ (96 to 98 percent); pure $H_2O$ (100 percent). The relative humidity was measured with an "AIR-GUIDE" dial hygrometer placed in slightly larger chambers (15.5 cm dia, 4.0 cm high), filled with similar volumes of the same saturated salt solutions. In these chambers, the relative humidity stabilized within the desired range in three hours. In addition, the effect of free moisture was tested by maintaining test chambers at 100 percent relative humidity and placing a drop of water on top of each dead infected mite. Each test chamber was placed inside a large "ZIP-LOCK" plastic bag containing 50 ml of the proper salt solution to further guarantee a stable relative humidity.

In experiments evaluating environmental effects on the production of conidia, plastic microscope cover slips were cut into four equal pieces and placed in the center of relative humidity controlled test chambers. One dead infected mite was placed on each cover slip. Temperature was controlled by placing test chambers inside incubators.

Relative Humidity and Temperature Effects on Production of Primary Conidia

This experiment utilized a factorial design with relative humidity (75, 85, 98, 100 percent and free moisture) and temperature (4.4, 10.0, 15.6, 21.1, 26.7 and 32.2 degrees Centigrade) as the main effects. Infected cadavers were removed from cold storage and immediately transferred to cover slips in the center of test chambers as previously described. After a five-day sporulation period under each relative humidity and temperature condition, the fungus material was stained and mounted in a lactophenol-cotton blue solution. The total number of primary conidia and capillaconidia were then counted.

Relative Humidity and Temperature Effects on Production of Capillaconidia

Infected mite cadavers were placed on cover slips in 100 percent relative humidity chambers at 21.1 degrees Centigrade for 24 hours. The cadavers were then removed, leaving a field of primary conidia. Ten control preparations were removed at 24 hours to determine the base line percentage of primary conidia that had already germinated and formed capillaconidia. The cover slips with primary conidia were then placed under the various temperature and relative humidity conditions described in the previous experiment. After five days, the number of primary conidia and capillaconidia were counted.

Effect of Temperature and Mite Movement on Infection

Two infected cadavers were placed two cm apart on each of 48 bean leaf squares (each square=14.4 cm$^2$). The leaf squares with cadavers were placed in test chambers held at 21.1 degrees Centigrade and 100 percent relative humidity for 48 hours. The cadavers were then removed and 20 adult female mites were added to each square on the leaf side opposite a previously established field of conidia. The conidia on each leaf square were exposed to lab conditions (25 degrees Centigrade, 30 percent relative humidity) for 10 minutes during the transfer of mites. Leaf squares with conidia and mites were placed in incubators set at 10, 15.6, 21.1 and 26.7 degrees Centigrade where they were held at 90 to 95 percent relative humidity for 24 hours. The mites were then transferred to fresh leaf squares on an open lab bench (25 degrees Centigrade, 25 to 45 percent relative humidity) where infected mites produced distinct brown cadavers in five days.

The effect of temperature and mite movement on infection was also tested under low relative humidity conditions. In this test, the procedure was followed for the above experiment, except that after mites were added, the leaf squares with conidia were held at 25 to 35 percent relative humidity.

Effect of Temperature on the Period of Lethal Infection

Two mite cadavers were placed on each of 32 leaf discs, and the fungus was allowed to sporulate for 48 hours prior to adding about 50 adult female *T. urticae* to each disc for an additional 24 hours (at 100 percent relative humidity, 21.1 degrees Centigrade). Each mite-infested leaf disk was then placed on top of a fresh bean leaf square (14.4 cm$^2$) and held at 10.0, 15.6, 21.1, 26.7, 29.4, 32.2, 35.0 or 37.8 degrees Centigrade for the remainder of the experiment. The number of mites that died as a result of infection by *N. floridana* were recorded every 24 hours after exposure to capillaconidia. Mites killed by the pathogen were easily distinguished from other dead mites by their firm and golden brown appearance. The experiment was repeated from three to five times for each temperature.

Direct Effect of Precipitation on Epizootics

The effect of precipitation without a prolonged period of high relative humidity was compared to the effect of prolonged periods of high relative humidity without precipitation on the development of epizootics in the greenhouse. When corn plants reached the early 12-leaf stage, five mite-infested bean leaves were placed on the lower leaves of each of 30 corn plants. One week later, 30 live infected mites were released on leaf five of each plant. The plants were separated into precipitation, high humidity, and control groups one week after the infected mites were released. Precipitation treatments consisted of simulated rainfall applied through a garden sprinkler for 30 minutes at 5:00 p.m. on each weekday. Infested corn plants in the high humidity group were subjected to daily periods of approximately 100 percent relative humidity by covering the plants with a clear polyethylene sheet from 5:00 p.m. to 7:00 a.m. each weeknight. Control plants were watered each day without wetting the foliage. Greenhouse environmental conditions were recorded on a hygrothermograph throughout the experiment. All the leaves from one vertical half of each of four plants in each treatment were removed weekly for brushing with a J. G. H. Edwards mite brushing machine. The number of mites were counted on each plant and subsamples were collected weekly for mounting on microscope slides. The percent infected mites was determined for each plant by dissecting and examining 50 mites microscopically for the presence of hyphal bodies.

Results

Sporulation over a five-day period reflected a significant interaction between temperature and relative humidity ($p=0.001$; Table 2).

TABLE 2

Number of primary conidia produced by *N. floridana* in dead infected mites when they were held for five days under various temperature and relative humidity conditions.

| Temperature (°C.) | Relative humidity (%) | | | |
|---|---|---|---|---|
| | 75 | 85 | 98 | 100 |
| 10.0 | 0 | 0 | 831 | 1,858 |
| 15.6 | 0 | 0 | 1,065 | 2,986 |
| 21.1 | 0 | 0 | 1,326 | 3,241 |
| 26.7 | 0 | 0 | 1,354 | 1,558 |
| 32.2 | 0 | 0 | 0 | 0 |

No primary conidia were produced at any temperature when the relative humidity was held at 75 or 85 percent. Production of primary conidia varied with temperature at 98 and 100 percent relative humidity with the greatest numbers produced at 100 percent relative humidity when temperatures ranged from 10.0 to 26.7 degrees Centigrade. No conidia were produced after five days at 4.4 or 32.2 degrees Centigrade. Temperature and relative humidity requirements for the formation of capillaconidia were similar to the conditions required for the production of primary conidia (Table 3).

TABLE 3

Percent primary conidia that germinated to form infective capillaconidia under various temperature and relative humidity conditions by *N. floridana*.

| Temperature (°C.) | Relative humidity (%) | | |
|---|---|---|---|
| | 85 | 98 | 100 |
| 10.0 | 5.1 | 19.4 | 36.6 |
| 15.6 | 6.0 | 40.3 | 42.7 |

TABLE 3-continued

Percent primary conidia that germinated to form infective capillaconidia under various temperature and relative humidity conditions by *N. floridana*.

| Temperature (°C.) | Relative humidity (%) | | |
|---|---|---|---|
| | 85 | 98 | 100 |
| 21.1 | 6.8 | 35.9 | 48.4 |
| 26.7 | 6.2 | 17.0 | 7.9 |
| 29.4 | 3.1 | 2.5 | 10.0 |

The development of capillaconidia was also influenced by a significant temperature relative humidity interaction ($p=0.001$). The greatest number of capillaconidia developed at 100 percent relative humidity for all temperatures except 26.7 degrees Centigrade when more capillaconidia developed at 98 percent relative humidity. The low number of capillaconidia that developed at 26.7 degrees Centigrade and 100 percent relative humidity does not appear to be consistent with the rest of the data. We could not determine whether this inconsistency in the response surface represents a real environmental effect or an outlying data point. The increase in moisture at 100 percent relative humidity compared to 98 percent relative humidity was not as critical to the formation of capillaconidia as it was to the production of primary conidia. In both of these experiments, the number of conidia produced in free moisture treatments consistently averaged 20 to 50 percent less than the numbers produced in 100 percent relative humidity treatments for all temperatures. The reduction in numbers of conidia produced in free moisture treatments was most likely due to the submergence of infected mite cadavers in drops of water.

When mites were added to leaf squares maintained at 90 to 95 percent relative humidity and previously infested with capillaconidia, temperature and temperature-mediated mite movement had no significant effect on the incidence of mite infection. When this experiment was repeated under dry conditions (25 to 35 percent relative humidity), no mites became infected at any temperature. Apparently, relative humidity is more important than temperature in determining the longevity of previously established capillaconidia.

The average period of lethal infection (time from infection to mite death) was determined for each temperature from a cumulative mortality curve by calculating when 50 percent of the infected mites died. This period was shortest (3.8 days) at 25 to 32 degrees Centigrade. Infected mites took much longer to die at 37.8 (6.2 days) and 10 degrees Centigrade (16.1 days). The relationship of the mortality rate of infected mites (the inverse of the period of lethal infection) to temperature is a sigmoid curve due to high temperature inhibition of the fungus pathogen. Although data was not collected for all temperatures, we noticed that the total number of dead infected mites at 37.8 degrees Centigrade averaged only one half the number at 32 degrees Centigrade. This suggests that fungus development within mites was inhibited at temperatures above 32 degrees Centigrade.

The relative effects of 100 percent relative humidity and precipitation on the development of epizootics were determined in the greenhouse where the daily high and low temperatures were within the range of 32 to 38 and 16 to 20 degrees Centigrade, respectively. The relative humidity experienced by all corn plants except those covered with a plastic sheet ranged from 85 to 100 percent for about 10 hours each night and rarely remained at 100 percent for more than two hours. Precipitation alone without any associated period of high humidity was not enough to induce an epizootic of *N. floridana* (Table 4).

TABLE 4

Percent mites infected with *N. floridana* on greenhouse corn plants subjected to 30 minutes of simulated rain per day, 14 hours of 100 percent relative humidity per day, or neither (control).

| | Days after start of rain and relative humidity treatments | | | |
|---|---|---|---|---|
| | 0 | 7 | 14 | 21 |
| Rain | 1.0 ± 1.2[a] | 1.3 ± 0.8 | 0.4 ± 0.8 | 3.0 ± 3.4 |
| 100% Relative humidity periods | 0.4 ± 0.8 | 0.9 ± 1.0 | 65.0 ± 3.0 | 75.0 ± 6.8 |
| Control | 0 ± 0 | 0 ± 0 | 0 ± 0 | 0 ± 0 |

[a]Mean and standard deviation.

When corn plants infested with mites were subjected to 14-hour periods of 100 percent relative humidity each night, 65 percent of these mites became infected within 14 days, compared to a 1.4 percent infection of the mites on corn plants receiving 30 minutes of simulated rain per day without a prolonged period of high relative humidity. No mites were infected in the absence of rain and 100 percent relative humidity periods.

The present invention has been described in detail above, with the full range of our invention being pointed out by the claims set forth below. Those modifications of the invention which fall within the range of equivalents of the claims are to be included therein.

That which is claimed is:

1. In an agricultural field containing crop plants, which field is infested with both insects which do not significantly harm the crop plants and undesirable plant feeding mites, the method of selectively reducing the population of the plant feeding mites, comprising innoculating the field with an amount of the fungus *Neozygites floridana* effective to infect the plant feeding mites so that the plant feeding mites are selectively killed without substantially infecting the insects which are not harmful to the crop plants.

2. A method according to claim 1, wherein said plant feeding mites belong to the Family Tetranychidae.

3. A method according to claim 2, wherein said plant feeding mites belong to the group consisting of Genus Eotetranychus, Genus Eutetranychus, Genus Panonychus, Genus Oligonychus, and Genus Tetranychus.

4. A method according to claim 2, wherein said plant feeding mites are Six-spotted spider mites (*Eotetranychus sexmaculatus*).

5. A method according to claim 2, wherein said plant feeding mites are Texas citrus mites (*Eutetranychus banksi*).

6. A method according to claim 2, wherein said plant feeding mites are Citrus red mites (*Panonychus citri*).

7. A method according to claim 2, wherein said plant feeding mites are European red mites (*Panonychus ulmi*).

8. A method according to claim 2, wherein said plant feeding mites are McDaniel mites (*Tetranychus mcdanieli*).

9. A method according to claim 2, wherein said plant feeding mites are Pacific spider mites (*Tetranychus pacificus*).

10. A method according to claim 2, wherein said plant feeding mites are Strawberry spider mites (*Tetranychus turkestani*).

11. A method according to claim 2, wherein said plant feeding mites are Twospotted spider mites (*Tetranychus urticae*).

12. A method according to claim 2, wherein said plant feeding mites are Spruce spider mites (*Oligonychus ununguis*).

13. A method according to claim 2, wherein said plant feeding mites are Sugi spider mites (*Oligonychus hondoensis*).

14. A method according to claim 2, wherein said plant feeding mites are of the species *Tetranychus evansi*.

15. A method according to claim 1, wherein said fungus is applied to the crop plants in the form of insect mummies containing the fungus.

16. In an agricultural field containing crop plants, which field is infested with both insects which do not significantly harm the crop plants and undesirable Twospotted spider mites (*Tetranychus urticae*), the method of selectively reducing the population of the Twospotted spider mites, comprising innoculating the field with an amount of the fungus *Neozygites floridana* effective to infect the Twospotted spider mites by spraying the crop plants with an aqueous suspension of insect mummies containing the fungus, so that the Twospotted spider mites are selectively killed without substantially infecting the insects which are not harmful to the crop plants.

* * * * *